US007186844B2

United States Patent
Ikemoto

(10) Patent No.: US 7,186,844 B2
(45) Date of Patent: Mar. 6, 2007

(54) METHOD FOR PRODUCING CYCLIC CARBAMATE ESTER

(75) Inventor: Kazuto Ikemoto, Niigata (JP)

(73) Assignee: Mitsubishi Gas Chemical Co., Inc., Tokyo (JP)

( * ) Notice: Subject to any disclaimer, the term of this patent is extended or adjusted under 35 U.S.C. 154(b) by 276 days.

(21) Appl. No.: 11/025,934

(22) Filed: Jan. 3, 2005

(65) Prior Publication Data

US 2005/0154200 A1   Jul. 14, 2005

(30) Foreign Application Priority Data

Jan. 13, 2004   (JP)   ............................ 2004-005353

(51) Int. Cl.
*C07D 263/00*   (2006.01)
*C07D 221/22*   (2006.01)
(52) U.S. Cl. ....................................... 548/229; 546/97
(58) Field of Classification Search ................ 548/229; 546/97
See application file for complete search history.

(56) References Cited

U.S. PATENT DOCUMENTS 6,531,470 B1 *   3/2003   Gordeev et al. ......... 514/236.8
6,635,769 B1 *   10/2003   Blass ......................... 548/229
6,716,980 B2 *   4/2004   Pearlman .................... 544/137
6,887,995 B2 *   5/2005   Perrault et al. ............ 544/58.2
6,909,005 B1 *   6/2005   Patel .......................... 548/229
7,002,020 B1 *   2/2006   Gordeev et al. ............ 548/231
7,034,017 B2 *   4/2006   Straub et al. ............ 514/230.8
7,087,784 B2 *   8/2006   Perrault et al. ............. 564/224
7,094,900 B2 *   8/2006   Gadwood et al. ........... 546/209

FOREIGN PATENT DOCUMENTS

| JP | 49-116058 | 11/1974 |
| JP | 59-222481 | 12/1984 |
| JP | 7-59570 | 6/1995 |
| JP | 2002-105064 | 4/2002 |
| JP | 203-64062 | 3/2003 |
| JP | 2003-96058 | 4/2003 |

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

A method for producing a cyclic carbamate ester produces the cyclic carbamate ester by reacting an organic compound having at least two halogen atoms per molecule, an amine having at least two hydrogen atoms on a nitrogen atom, and carbon dioxide.

5 Claims, No Drawings

METHOD FOR PRODUCING CYCLIC CARBAMATE ESTER

BACKGROUND OF THE INVENTION

1. Field of the Invention

The present invention relates to a method for producing a cyclic carbamate ester. More particularly, the present invention relates to a method for efficiently producing a cyclic carbamate ester by conducting a reaction using, as starting materials, an organic compound having at least two halogen atoms per molecule, an amine having at least two hydrogen atoms on a nitrogen atom, and carbon dioxide.

Priority is claimed on Japanese Patent Application No. 2004-005353, filed Jan. 13, 2004, the content of which is incorporated herein by reference.

2. Description of Related Art

A cyclic carbamate ester is used as an electrolytic solution in batteries, condensers and capacitors, or is used for cleaning semiconductors. Also, it is used as medicines such as antibiotics.

As a method for producing a cyclic carbamate ester, for example, a method of using an amino alcohol and phosgene is described in Japanese Unexamined Patent Application, First Publication No. Hei 7-59570. Also, a method of using the-amino alcohol, as starting materials, and carbon monoxide, dimethyl carbonate or ethylene carbonate is described in Japanese Examined Patent Application, Second Publication No. Sho 49-116058, Japanese Unexamined Patent Application, First Publication No. Sho 59-222481 and Japanese Unexamined Patent Application, First Publication No. 2002-1050648 respectively. As a method taking account of environmental problems, the reaction of non-toxic carbon dioxide and the amino alcohol is described in Japanese Unexamined Patent Application, First Publication No. 2003-64062, and the reaction of non-toxic carbon dioxide and a cyclic amine is described in Japanese Unexamined Patent Application, First Publication No. 2003-96058.

However, because phosgene is a deadly poison, in the case of a method for producing a cyclic carbamate ester using the phosgene, there is a drawback such as limitation in location and the need for safety equipment of the plant for producing a cyclic carbamate. In the case of using the amino alcohol as the starting material, there are drawbacks that the amino alcohol is expensive and that a substitution product of the cyclic carbamate ester must be produced from the amino alcohol. In the case of using carbon dioxide, the same drawback exists when the amino alcohol is used as the starting material, and expensive reagents such as dehydrating agent is required. In the case of using a material having an aziridine structure as the starting material, the material often has high toxicity and has drawbacks in that it is not easily synthesized and is expensive.

In the method for producing a cyclic carbamate ester, effective utilization of cheap and non-toxic carbon dioxide is required. The method for producing a carbamate ester without using an expensive amino alcohol has been scarcely proposed and it has hitherto been required to develop the method. An object of the present invention is to provide the method for producing a cyclic carbamate ester in a safe and inexpensive manner by using the inexpensive and non-toxic carbon dioxide without using an expensive amino alcohol as a starting material of a cyclic skeleton.

SUMMARY OF THE INVENTION

The present inventors have intensively researched the method for producing a cyclic carbamate ester, which satisfies these above conditions, and thus the present invention has been completed. An aspect of the present invention is directed to a method for producing a cyclic carbamate ester represented by the general formula (1), comprising the step of conducting a reaction using, as starting materials, an organic compound represented by the general formula (2) or (3) which has at least two halogen atoms per molecule, an amine represented by the general formula (4), and carbon dioxide,

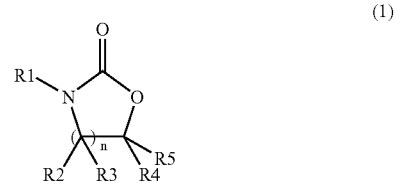

(1)

wherein R1, R2, R3, R4 and R5 may be the same or different groups or be linked cyclic groups and represent a non-substituted or substituted aryl group, hydrogen, a hydroxyl group, an alkyl group having 1 to 12 carbon atoms which has at least one halogen or at least one substituent, an alkenyl group, an alkynyl group or a cycloalkyl group, and the substituent represents an aryl group, an alkyl group, an alkenyl group, an alkynyl group, an alkoxy group, a carbonyl group, a carboxyl group, a hydroxyl group, a mercapto group, a halogen, a sulfonyl group or an amino group; and n represents an integer satisfying the following relationship: $0 \leq n \leq 4$,

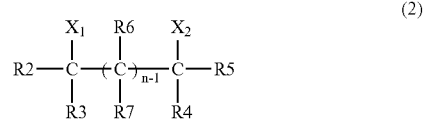

(2)

wherein $X_1$ and $X_2$ represent a halogen atom and may be the same or different halogen atoms; R2, R3, R4, R5, R6 and R7 may be the same or different groups or be linked cyclic groups and represent a non-substituted or substituted aryl group, hydrogen, a hydroxyl group, an alkyl group having 1 to 12 carbon atoms which has at least one halogen or at least one substituent, an alkenyl group, an alkynyl group or a cycloalkyl group, and the substituent represents an aryl group, an alkyl group, an alkenyl group, an alkynyl group, an alkoxy group, a carbonyl group, a carboxyl group, a hydroxyl group, a mercapto group, a halogen, a sulfonyl group or an amino group; and n represents an integer satisfying the following relationship: $1 \leq n \leq 4$,

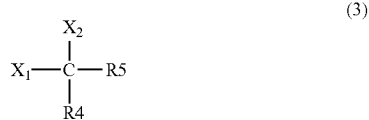

(3)

wherein $X_1$ and $X_2$ represent a halogen atom and may be the same or different halogen atoms; and R4 and R5 are as defined above,

(4)

wherein R1 is as defined above.

In the present invention, the cyclic carbamate ester may be a 5- or 6-membered cyclic carbamate ester, and the reaction is conducted at a temperature within a range of 10 to 350° C., and the cyclic carbamate ester may be N-methyl-2-oxazolidinone, 3-methyl-1,3-oxazinan-2-one, 3,4-dimethyl-1,3-oxazolidin-2-one, 3,5-dimethyl-1,3-oxazolidin-2-one, 2-oxazolidinone, 4-phenyl-2-oxazolidinone, 4,5-diphenyl-2-oxazolidinone, 5-methyl-2-oxazolidinone or N-phenyl-2-oxazolidinone, and a cyclic urea is simultaneously produced.

According to the present invention, it is made possible to produce a cyclic carbamate ester in a safe and inexpensive manner by using, as starting materials, inexpensive and non-toxic carbon dioxide, an organic compound having at least two halogen atoms in the molecule, and an amine having at least two hydrogen atoms on a nitrogen atom without having to use deadly poisonous phosgene.

DETAILED DESCRIPTION OF THE INVENTION

The embodiments of the method for producing a cyclic carbamate ester compound of the present invention will now be described in detail. The present invention is directed to the method for producing a cyclic carbamate ester, comprising the step of conducting a reaction using, as starting materials, an organic compound having at least two halogen atoms in the molecule, an amine having at least two hydrogen atoms on a nitrogen atom, and carbon dioxide. The cyclic carbamate ester to be produced is not specifically limited as long as it is cyclic, and the 4- to 8-membered cyclic carbamate esters are preferable because of their wide use. In particular, the cyclic carbamate ester having a 5-membered ring is preferable and a compound represented by the general formula (5) is preferable:

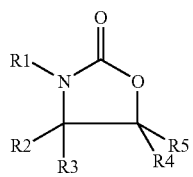

(5)

wherein R1, R2, R3, R4 and R5 are as defined above.

Specific examples of the 5-membered carbamate ester include N-methyl-2-oxazolidinone, 3-methyl-1,3-oxazinan-2-one, 3,4-dimethyl-1,3-oxazolidin-2-one, 3,5-dimethyl-1,3-oxazolidin-2-one, 2-oxazolidinone, 4-phenyl-2-oxazolidinone, 4,5-diphenyl-2-oxazolidinone, 5-methyl-2-oxazolidinone and N-phenyl-2-oxazolidinone.

Also, the 6-membered cyclic carbamate ester is preferable and is a compound represented by the general formula (6):

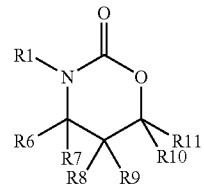

(6)

wherein R1, R6, R7, R8, R9, R10 and R11 may be the same or different groups or be linked cyclic groups and represent a non-substituted or substituted aryl group, hydrogen, a hydroxyl group, an alkyl group having 1 to 12 carbon atoms which has at least one halogen or at least one substituent, an alkynyl group, a cycloalkyl group or hydrogen, and the substituent represents an aryl group, an alkyl group, an alkenyl group, an alkynyl group, an alkoxy group, a carbonyl group, a carboxyl group, a hydroxyl group, a mercapto group, a halogen, a sulfonyl group or an amino group.

Specific examples of the 6-membered carbamate ester include alkyl-[1,3]-2-oxazinanone such as [1,3]-2-oxazinanone, methyl-[1,3]-2-oxazinanone, N-methyl-[1,3]-2-oxazinanone, dimethyl-[1,3]-2-oxazinanone, phenyl-[1,3]-2-oxazinanone, N-phenyl-[1,3]-2-oxazinanone, or diphenyl-[1,3]-2-oxazinanone.

The halogen-containing organic compound, one of the starting materials used in the present invention, is not specifically limited as long as it is a compound represented by the general formula (2) or (3) which has at least two halogen atoms per molecule. Particularly preferably, the halogen atom is any of a chlorine atom, a bromine atom and an iodine atom.

Specific examples of the compound represented by the general formula (2) include 1,2-dichloroethane, 1,2-dibromoethane, 1,2-diiodoethane, 1,2-dichloropropane, 1,2-dibromopropane, 1,2-diiodopropane, 1,2-dichlorobutane, 1,2-dibromobutane, 1,2-diiodobutane, 1,3-dichloropropane, 1,3-dibromopropane, 1,3-diiodopropane, 1,1,2-trichloroethane, 1,1,2,2-tetrachloroethane, hexachloroethane and 1,4-dichlorobutane. Specific examples of the compound represented by the general formula (3) include dichloromethane, chloroform, carbon tetrachloride, dibromomethane, bromoform, carbon tetrabromide, diiodomethane and iodoform. In the present invention, the halogen-containing organic compound is not limited to these examples and may be any organic compound having two or more halogen atoms.

The amine, one of the starting materials used in the present invention, is represented by the general formula (4) and is not specifically limited as long as it has at least two hydrogen atoms on a nitrogen atom. Primary amines, ammonia, hydrazine and hydroxylamines can be used.

Specific examples of the amine include methylamine, ethylamine, n-propylamine, isopropylamine-n-butylamine, sec-butylamine, isobutylamine, t-butylamine, pentylamine, 2-aminopentane, 3-aminopentane, 1-amino-2-methylbutane, 2-amino-2-methylbutane, 3-amino-2-methylbutane, 4-amino-2-methylbutane, hexylamine, 5-amino-2-methylpentane, heptylamine, octylamine, nonylamine, decylamine, undecylamine, dodecylamine, tridecylamine, tetradecylamine, pentadecylamine, hexadecylamine, heptadecylamine, octadecylamine, ethanolamine, isopropanolamine, 1-aminopropan-3-ol, 1-aminobutan-2-ol, 2-aminobutan-1-ol, 3-aminobutan-1-ol, 1-aminobutan-4-ol, 1-amino-2-methylpropan-2-ol, 2-amino-2-methylpropan-1-ol, 1-aminopentan-4-ol, 2-amino-4-methylpentan-1-ol, 2-aminohexan-1-ol, 3-aminoheptan-4-ol, 1-aminooctan-2-ol, 5-aminooctan-4-ol, 1-aminopropane-2,3-diol, 2-aminopropane-1,3-diol, tris(oxymethyl)aminomethane, 1,2-diaminopropan-3-ol, 1,3-diaminopropan-2-ol, 2-(2-aminoethoxy)ethanol, ethylenediamine, propylenediamine, butylenediamine, trimethylenediamine, tetramethylenediamine, 1,3-diaminobutane, 2,3-diaminobutane, pentamethylenediamine, 2,4-diaminopentane, hexamethylenediamine, heptamethylenediamine, octamethylenediamine, nonamethylenediamine, N-ethylethylenediamine, N,N-diethylethylenediamine, triethylethylenediamine, 1,2,3-triaminopropane, tris(2-aminoethyl)amine, tetra(aminomethyl)methane, diethylenetriamine, triethylenetetramine, tetraethylpentamine, heptaethyleneoctamine, hydroxylamine and O-methylhydroxylamine.

The carbon dioxide as one of starting materials used in the present invention may be supplied in the form of carbonate, hydrogen carbonate or carbamate. The carbon dioxide exists in the form of carbonate, hydrogen carbonate or carbamate under alkaline conditions and can be used in this form without causing any problem in the present invention. Specific examples of the form to be supplied for the reaction include carbon dioxide gas, liquefied carbon dioxide, amine carbonate, amine hydrogen carbonate, amine carbamate, alkali metal carbonate, alkali metal hydrogen carbonate, alkali metal carbamate, alkaline earth carbonate, alkaline earth hydrogen carbonate and alkaline earth carbamate. The carbon dioxide may be supplied in these forms.

The reaction temperature varies depending on the structure, molar ratio of starting materials and the kind of the solvent and is therefore appropriately selected. The reaction temperature is preferably within a range of 10 to 350° C., more preferably within a range of 60 to 250° C., and most preferably within a range of 120 to 160° C. The phase of the reaction may be any of a liquid phase, a vapor phase and a supercritical phase and is not specifically limited.

The reaction time is not specifically limited and is preferably within a range of 0.01 to 48 hours, more preferably within a range of 0.1 to 12 hours, and most preferably within a range of 1 to 4 hours taking account of industrial production. The reaction pressure may be normal pressure, increased pressure and reduced pressure and is not specifically limited as long as carbon dioxide is absorbed in the other reactants and reacted. The reaction pressure is preferably within a range of 0.1 to 30 MPa, more preferably within a range of 0.1 to 6 MPa, and most preferably within a range of 0.1 to 1 MPa taking account of industrial production.

The method for producing cyclic carbamate ester in the present invention can be carried out in any of batchwise, semi-batchwise and continuous systems. During the reaction, a solvent can be used. As the solvent, water, an amine compound, an alcohol compound, an ether compound and an amide compound are used easily. Water, an alcohol compound and an ether compound are particularly preferable.

The reaction mechanism in the method for producing a cyclic carbamate ester is the desalting reaction from the halogen-containing organic compound, and a cyclic carbamate ester is produced as the reaction proceeds. The hydrogen halide produced during the reaction can be taken out in the acid form, the form of a salt with the amine used, or the form of a salt of an alkaline compound. To take out the hydrogen halide in the form of a salt of an alkaline compound, an alkaline compound can be added in the reaction without causing any problem. For example, no problem occurs even when alkaline hydroxide, carbonate and bicarbonate are added. Although the reaction proceeds in the absence of a catalyst, the catalyst can be added, if necessary. Either homogeneous or heterogeneous catalyst can be used. Transition metal catalyst, complex catalyst, metal ion, metal oxide and enzyme can be used without causing any problem. After the reaction, the cyclic carbamate ester can be purified by the method such as extraction, distillation, recrystallization or chromatography. In the present invention, any method for purification can be used and is not specifically limited.

In the present invention, a cyclic urea can be produced simultaneously by varying the reaction temperature, the reaction time, the reaction pressure and the molar ratio. The cyclic urea can be produced by further reacting the cyclic carbamate ester with an amine. In the case of simultaneously producing a cyclic urea, the reaction may be conducted at a temperature which is higher than that in the case of producing the cyclic carbamate ester alone by 10° C. or more, preferably 20° C. or more. Specifically, the reaction is preferably conducted at a temperature within a range of 30 to 400° C., more preferably within a range of 80 to 290° C., and most preferably within a range of 140 to 180° C. In the case of simultaneous production, the product ratio of the cyclic urea to the cyclic carbamate ester can be increased by conducting the reaction for a long time as compared with the case of producing the cyclic carbamate ester alone. Therefore, the reaction time may be appropriately selected according to the required amounts of the products. In that case, the extra reaction time is within a range from 10 minutes to 48 hours. To produce a large amount of the cyclic urea, the molar ratio of the amine and the halogen-containing compound which are starting materials (amine/halogen-containing compound) may be increased. The molar ratio of amine to the halogen-containing compound is preferably from 2 to 100, more preferably from 3 to 50, and most preferably from 4 to 10. The reaction pressure is secondarily, that is dependently, decided by the composition ratio of starting materials and reaction temperature. The cyclic urea is important as a solvent for production of medicines, a reaction intermediate, and an electrolytic solution in batteries, condensers and capacitors. In the present invention, there is an advantage that the product ratio of cyclic carbamate ester and the cyclic urea can vary by changing these conditions, as described above.

EXAMPLES

Examples of the present invention will now be described. The following examples further illustrate the present invention in detail, and the present invention is not limited to the examples as long as it does not depart from the spirit of the present invention.

Example 1

1 g of 1,2-dichloroethane and 5.5 g of an aqueous 40% methylamine solution were charged in a 20 ml pressure vessel made of SUS316 and 1.9 g of a carbon dioxide gas was absorbed under a pressure of 0.5 MPa, followed by heating at 120° C. for 2 hours. After cooling the pressure vessel, the contents were removed and analyzed by gas chromatography. As a result, N-methyl-2-oxazolidinone was obtained in a 94% yield based on 1,2-dichloroethane. Hydrogen chloride produced, as a by-product, during the reaction was neutralized with excess amine.

Example 2

The following experiments were carried out in the same manner as in Example 1. 1 g of 1,2-dichloroethane and 5.3 g of 40% a methylamine solution in methanol were charged in a 20 ml pressure vessel made of SUS316 and 2.7 g of a carbon dioxide gas was absorbed under a pressure of about 0.5 MPa, followed by heating at 160° C. for 3 hours. As a result, N-methyl-2-oxazolidinone was obtained in a 6% yield and N,N'-dimethylimidazolidinone was obtained in a 23% yield.

Example 3

1.24 g of 1,3-dichloropropane and 5.15 g of a 40% methylamine aqueous solution were charged in a 20 ml pressure vessel made of SUS316 and 1.95 g of a carbon dioxide gas was absorbed under a pressure of about 0.5 MPa, followed by heating at 120° C. for 2 hours. As a result, 3-methyl-1,3-oxazinan-2-one was obtained in a 15% yield and 1,3-dimethyltetrahydropyrimidin-2(1H)-one was obtained in a 64% yield.

Example 4

1.10 g of 1,2-dichloropropane and 7.18 g of a 40% methylamine aqueous solution were charged in a 20 ml pressure vessel made of SUS316 and 2.11 g of a carbon dioxide gas was absorbed under a pressure of about 0.5 MPa, followed by heating at 160° C. for 4 hours. As a result, 3,4-dimethyl-1,3-oxazolidin-2-one and 3,5-dimethyl-1,3-oxazolidin-2-one were obtained in a total yield of 64% and 1,3,4-trimethylimidazolidin-2-one was obtained in a 23% yield.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method for producing a cyclic carbamate ester represented by the general formula (1), comprising the step of conducting a reaction using, as starting materials, an organic compound represented by the general formula (2) or (3) which has at least two halogen atoms per molecule, an amine represented by the general formula (4), and carbon dioxide,

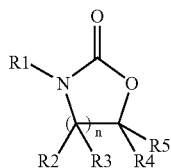 (1)

wherein R1, R2, R3, R4 and R5 may be the same or different groups or be linked cyclic groups and represent a non-substituted or substituted aryl group, hydrogen, a hydroxyl group, an alkyl group having 1 to 12 carbon atoms which has at least one halogen or at least one substituent, an alkenyl group, an alkynyl group or a cycloalkyl group, and the substituent represents an aryl group, an alkyl group, an alkenyl group, an alkynyl group, an alkoxy group, a carbonyl group, a carboxyl group, a hydroxyl group, a mercapto group, a halogen, a sulfonyl group or an amino group; and n represents an integer satisfying the following relationship: $0 \leq n \leq 4$,

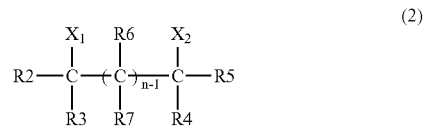 (2)

wherein $X_1$ and $X_2$ represent a halogen atom and may be the same or different halogen atoms; R2, R3, R4, R5, R6 and R7 may be the same or different groups or be linked cyclic groups and represent a non-substituted or substituted aryl group, hydrogen, a hydroxyl group, an alkyl group having 1 to 12 carbon atoms which has at least one halogen or at least one substituent, an alkenyl group, an alkynyl group or a cycloalkyl group, and the substituent represents an aryl group, an alkyl group, an alkenyl group, an alkynyl group, an alkoxy group, a carbonyl group, a carboxyl group, a hydroxyl group, a mercapto group, a halogen, a sulfonyl group or an amino group; and n represents an integer satisfying the following relationship: $1 \leq n \leq 4$,

 (3)

wherein $X_1$ and $X_2$ represent a halogen atom and may be the same or different halogen atoms; and R4 and R5 are as defined above,

 (4)

wherein R1 is as defined above.

2. The method for producing a cyclic carbamate ester according to claim 1, wherein the cyclic carbamate ester is a 5- or 6-membered cyclic carbamate ester.

3. The method for producing a cyclic carbamate ester according to claim 1, wherein the reaction is conducted at a temperature within a range of 10 to 350° C.

4. The method for producing a cyclic carbamate ester according to claim 1, wherein the cyclic carbamate ester is N-methyl-2-oxazolidinone, 3-methyl-1,3-oxazinan-2-one, 3,4-dimethyl-1,3-oxazolidin-2-one, 3,5-dimethyl-1,3-oxazolidin-2-one, 2-oxazolidinone, 4-phenyl-2-oxazolidinone, 4,5-diphenyl-2-oxazolidinone, 5-methyl-2-oxazolidinone or N-phenyl-2-oxazolidinone.

5. The method for producing a cyclic carbamate ester according to claim 1, wherein a cyclic urea is simultaneously produced.

* * * * *